US007179485B1

(12) United States Patent
Schneider et al.

(10) Patent No.: US 7,179,485 B1
(45) Date of Patent: Feb. 20, 2007

(54) HOLLOW CAPSULE HAVING A WALL PERMEABLE TO WATER OR AN AQUEOUS SOLUTION

(75) Inventors: John H. Schneider, Richardson, TX (US); Steven B. Laramay, Mesquite, TX (US)

(73) Assignee: Fritz Industries, Inc A Texas Corporation, Mesquite, TX (US)

( * ) Notice: Subject to any disclaimer, the term of this patent is extended or adjusted under 35 U.S.C. 154(b) by 1014 days.

(21) Appl. No.: 09/770,931

(22) Filed: Jan. 26, 2001

(51) Int. Cl.
*A61K 9/48* (2006.01)
*C08F 287/00* (2006.01)
*C11D 17/00* (2006.01)

(52) U.S. Cl. ....................... 424/451; 524/457; 510/513

(58) Field of Classification Search ................ 424/451; 252/95; 524/457; 526/217; 428/423.1; 510/513
See application file for complete search history.

(56) References Cited

U.S. PATENT DOCUMENTS

| | | | | |
|---|---|---|---|---|
| 4,741,401 | A | 5/1988 | Walles et al. | 166/300 |
| 4,756,844 | A | 7/1988 | Walles et al. | 252/95 |
| 4,919,209 | A | 4/1990 | King | 166/300 |
| 4,923,753 | A | 5/1990 | Walles et al. | 428/402.24 |
| 5,173,526 | A | 12/1992 | Vijayendran et al. | 524/457 |
| 5,373,901 | A | 12/1994 | Norman et al. | 166/300 |
| 5,741,433 | A * | 4/1998 | Mitchell et al. | 252/74 |
| 5,948,735 | A * | 9/1999 | Newlove et al. | 507/238 |
| 6,436,540 | B1 * | 8/2002 | Garcia et al. | 428/423.1 |

* cited by examiner

*Primary Examiner*—Sreeni Padmanabhan
*Assistant Examiner*—Gina C. Yu
(74) *Attorney, Agent, or Firm*—Thomas R. Weaver

(57) ABSTRACT

This invention discloses, as an article of manufacture, a capsule having a hollow interior and an enclosing wall, referred to as a membrane. The membrane is not soluble in water, but is permeable to water or an aqueous solution. The membrane is comprised of a first material and can also include a second material. When the membrane is comprised of the first material and the second material, then it is referred to as a composite material wherein the first material forms sporting matrix having the second material fixed in the matrix. The first material is a urethane/vinyl hybrid polymer and is not soluble in, reactive with or a solvent for the second material. The second material is a particulate solid, different from the first material, and is not soluble in, reactive with or a solvent for the first material. The capsule of this invention is useful to maintain in the hollow interior thereof a solid, water-soluble first chemical composition which is not soluble in, reactive with or a solvent for the enclosing wall of the capsule. In operation, the exterior of the capsule, having the first composition maintained in the interior thereof, is placed in contact with a water-soluble second chemical composition which is not soluble in, reactive with or a solvent for the enclosing wall of the capsule, but which is reactive with the first chemical composition.

19 Claims, No Drawings

HOLLOW CAPSULE HAVING A WALL PERMEABLE TO WATER OR AN AQUEOUS SOLUTION

BACKGROUND OF THE INVENTION

1. Technical Field of the Invention

This invention broadly relates to a capsule comprised of a chemical composition surrounded by an exterior protective coating. The invention more particularly relates to the material employed to produce the exterior protective coating which surrounds the chemical composition contained in the capsule. The invention further relates to the release of the composition from the capsule.

2. Description of the Prior Art and Problems Solved

The prior art has long dealt with the problem of causing, or of creating the conditions to cause, a specified chemical composition to react in a specified environment or in a specified location at a specified time or over a specified period of time. This problem ordinarily stems from the need to initiate some chemical action in some desirable location prior to the start of, during or subsequent to the completion of some other action, and/or to cause the chemical action associated with a specified chemical composition to proceed over a desirable period of time. The related problems of controlling the time and controlling the place of reaction of a composition, as well as the solutions thereto, have been variously referred to in the art as delayed release, continuous release and controlled release and are referred to as such herein.

The prior art has addressed the problems referred to above and has developed various methods of controlling the introduction of an active chemical composition into reactive contact with an environment. The solutions to the problems have necessarily involved preventing reactive contact of the active chemical composition with an environment followed by enabling reactive contact to occur at some later time. One of the methods developed features the steps of preventing the mentioned reactive contact by completely covering a small quantity of the active chemical composition with a material to produce a capsule containing the composition followed by introducing a number of such capsules into a designated environment wherein the composition is released from the capsule to enable reactive contact to thereby produce a desired chemical action.

The mode of release of the active chemical composition into reactive contact with the environment as contemplated by the prior art has proceeded along various different mechanisms. Such release mechanisms range from external crushing forces applied to the confining material, internal rupture and bursting forces applied to the confining material, disintegration of the confining material and diffusion or permeation of liquid through the confining material. Accordingly, the release mechanisms employed have featured the use of capsules which are crushed to rapidly release the enclosed chemical composition; capsules which rupture, or burst, to rapidly release the enclosed chemical composition; capsules which dissolve or disintegrate to rapidly release the enclosed composition; and capsules which do not rupture, but rely on diffusion or permeation, to gradually release the enclosed composition.

Chemical compositions known to have been involved in the controlled release thereof from a capsule have included medicines, pesticides, herbicides, cosmetics, laundry products, pigments, polymerization initiators, cross linking agents and viscosity reducing agents. A delayed and/or a continuous release of such compositions from enclosing capsules can offer the advantage of maximizing the effectiveness of the compositions or of minimizing or eliminating undesirable chemical or physical results or both.

The essential differences between the various controlled release methods of the prior art have resided in the nature of the material employed to form the exterior protective coating and the specific mechanism of the controlled release of the chemical composition from the confining material. Examples of such prior art methods are disclosed in various United States Patents including U.S. Pat. No. 4,756,844 (WALLES I), U.S. Pat. No. 4,741,401 (WALLES II), U.S. Pat. No. 4,923,753 (WALLES III), U.S. Pat. No. 4,919,209 (KING) and U.S. Pat. No. 5,373,901 (NORMAN et al).

The prior art patents referred to above all disclose capsules containing active chemical compositions and the methods, that is, the mechanisms, of releasing the compositions from the capsules to enable the encapsulated chemicals to react with a composition in contact with the exterior of the capsules. Walles I illustrates its invention in terms of an encapsulated bleach as a laundry detergent additive. Walles II, King and Norman et al illustrate their inventions in terms of an encapsulated breaker for a fracturing fluid in a subterranean formation. Walles III illustrates its invention in terms of an encapsulated acid. The chemical compositions disclosed range from those which treat water based liquids to those which treat oil based liquids. Furthermore, the release mechanisms disclosed and/or referred to range from capsules which are crushed to rapidly release the enclosed agent; capsules which rupture, or burst, to rapidly release the enclosed agent; capsules which do not rupture, but rely on diffusion or permeation, to gradually release the enclosed agent; and capsules which dissolve or disintegrate to rapidly release the enclosed agent.

An important, if not the essential, feature of a method of controlling the release of a composition from a capsule is the timing of the release. This feature can be conveniently illustrated in connection with the release of a chemical from a capsule to reduce the viscosity of a fracturing fluid subsequent to the performance of a fracturing treatment of a subterranean formation. Reducing the viscosity of a fracturing fluid is referred to in the art as "breaking" and the viscosity reducing chemical is referred to as a "breaker." For purposes well known in the fracturing art, it is desirable that a fracturing fluid have a high viscosity during the performance of the fracturing process, but a low viscosity subsequent to the performance of the process. In this regard, a desired high viscosity is preferably to be observed in the vicinity of the subterranean formation to be treated and a desired low viscosity is also preferably to be observed in the vicinity of the subterranean formation, wherein the high viscosity condition occurs prior to and during the performance of the fracturing treatment and the low viscosity condition occurs subsequent to the performance of the fracturing treatment.

Breakers, upon reactive contact with the fracturing fluid, can effectively produce the desired reduction of viscosity of the fluid, but the timing of the break, that is, when the break occurs, is of critical importance. Breakers, upon reactive contact with the fracturing fluid, begin to reduce the viscosity of the fluid. Accordingly, the problem to be solved is how to intimately mix the breaker with the fracturing fluid to enable essential reactive contact with the fluid, while at the same time delaying the time of reactive contact. This problem has been addressed and solved by placing the breaker in an enclosed volume called a capsule, the wall of which is a membrane which shields the fluid from the breaker to prevent reactive contact. The capsule containing the breaker is then intimately mixed with the high viscosity fluid, and the membrane, by one of the mentioned mechanisms, functions to release the breaker to enable reactive contact between the breaker and the fluid at some future time. The breaking of fracturing fluids and the use of encapsulated breakers to perform the task are subjects discussed in Norman et al, U.S. Pat. No. 5,373,901.

An important property of the material of construction of a capsule membrane is its ability to resist a caustic environment, either acid or base, exhibited by the chemical enclosed in, and thus in contact with, the interior of the capsule and by the chemical in contact with the exterior of the capsule. The sensitivity of the material of construction to a caustic environment is the subject of the disclosure of U.S. Pat. No. 4,923,753 (WALLES III) referred to above.

It is important from an operational point of view to be able to place chemical compositions of various natures, including caustic chemicals, in a capsule and to retain and maintain them therein shielded from the exterior environment until some desirable future time. A capsule thus constructed of a membrane material which will function to hold and maintain various diverse chemicals, such as, organic and inorganic caustics, salts and oxidizers, and which will also function to release the chemicals at some desirable time is desired by the art. Accordingly, the material of construction of the capsule coating is the principal issue addressed in this invention.

DISCLOSURE OF INVENTION

1. Summary of the Invention

This invention is an article of manufacture and a method of using the article to treat a chemical composition in contact with the exterior of the article. The article of this invention is, thus, a capsule comprised of a hollow interior and an enclosing wall which is permeable to water or an aqueous solution. A first, water-soluble, chemical composition is enclosed, that is, encapsulated, in the hollow interior of the capsule by the wall of the capsule.

The permeable wall of the capsule, which is referred to herein as a membrane, is at least comprised of a first material and can be comprised of the first material together with a second material, in which case, the membrane is a composite material. When the membrane is a composite material the first material forms a supporting matrix, and the second material is fixed in the supporting matrix.

The first material is a urethane/vinyl hybrid polymer. It is not reactive with, soluble in or a solvent for the encapsulated first chemical composition, the second material, the liquid in contact with the exterior surface of the membrane or the chemical composition (referred to herein and in the appended claims as the second chemical composition) in contact with the exterior of the membrane.

The second material is a particulate solid and is different from the first material. The second material is not reactive with, soluble in or a solvent for the encapsulated first chemical composition, the first material, the liquid in contact with the exterior surface of the membrane or the second chemical composition.

The encapsulated first chemical composition can be substantially any water-soluble material which is not reactive with, soluble in or a solvent for the first material or the second material, but is reactive with and is, thus, useful to alter the chemical and/or physical properties of the second chemical composition in contact with the exterior surface of the membrane. The chemical nature of the encapsulated first chemical composition can include enzymes, and organic and inorganic acids, bases, salts and oxidizing agents. The encapsulated first chemical compositions are useful as medicines, pesticides, algaecides, herbicides, cosmetics, laundry products, pigments, polymerization initiators, cross linking agents and viscosity reducing agents. The encapsulated first chemical composition can be an additive for adjusting the setting properties of hydraulic cement and can be a breaker for a fracturing fluid, wherein the breaker can be a chemical selected from water-soluble enzymes, and organic or inorganic acids, bases, salts and oxidizing agents.

The second chemical composition, which as disclosed, is in contact with the exterior surface of the membrane can be substantially any water-soluble material which is not reactive with, soluble in or a solvent for the first material or the second material, but is reactive with the encapsulated first chemical composition.

2. Description of the Preferred Embodiments

The article of this invention is a capsule comprised of a solid, water-soluble first chemical composition preferably enclosed, that is, encapsulated, in a composite material. The composite material is comprised of a first material, which forms a matrix, in combination with a second material, different from the first material, which is fixed in the matrix. The phrase "fixed in the matrix," when employed in connection with the second material, means that the second material, while being firmly attached to the matrix, can be completely embedded within and, therefor, completely surrounded by, the matrix, or it can be partially embedded within and partially exposed at the interior surface or at the exterior surface of the matrix. It is understood that the interior surface of the matrix is the interior surface of the membrane and the exterior surface of the matrix is the exterior surface of the membrane. As mentioned previously, the first material, which forms the supporting matrix of the membrane, is not reactive with, soluble in or a solvent for the encapsulated first chemical composition, the second material, the second chemical composition or a liquid in contact with the exterior surface of the membrane.

The first material is comprised of a urethane latex system and, more specifically, an aqueous polyurethane-vinyl polymer dispersion. The vinyl element preferred for use in this invention is acrylic in nature. Accordingly, the dispersion is more particularly referred to herein as a urethane/acrylic hybrid polymer. The aqueous polyurethane-vinyl polymer dispersion employed herein is disclosed in U.S. Pat. No. 5,173,526 to Vijayendran et al. According to Vijayendran et al, the polyurethane-vinyl polymer dispersion is prepared by the simultaneous polymerization of a vinyl monomer and chain extension of an isocyanate-terminated polyurethane prepolymer in the presence of water. More particularly, Vijayendran et al disclose that, "the aqueous polymer is prepared by (a) forming a carboxy-containing, water dispersible, isocyanate-terminated polyurethane prepolymer, (b) adding a vinyl monomer mixture which contains a polyethylenically unsaturated monomer to the prepolymer to make a prepolymer/monomer mixture, (c) adding a tertiary amine to the prepolymer/monomer mixture, (d) dispersing the prepolymer/monomer mixture in water, (e) adding an oil soluble free radical initiator and a chain extender to the aqueous dispersion, and (f) polymerizing the vinyl monomers and completing the chain extension of the prepolymer by heating the aqueous dispersion." The process is said to provide an intimacy of interaction that cannot be achieved by blending. Accordingly, the first material, as defined above, is not a mere blend of a polyurethane and an acrylic polymer.

A urethane/acrylic hybrid polymer dispersion useful herein is commercially available in the form of an aqueous polymer dispersion from Air Products and Chemicals, Inc., under the Hybridur family of trademarks, two of which are Hybridur 540 and Hybridur 580.

The aqueous polyurethane-vinyl polymer dispersion employed herein is disclosed in Vijayendran et al to be useful as a protective coating for a solid substrate. It is disclosed that the dispersion is applied to the substrate by conventional flexographic or gravure methods and that the finished product protects the substrate from solvents, corrodants, and abrasives and that it exhibits good gloss and flexibility. The mentioned solid substrates include paper, metals, plastics and wood.

The first material can also be a reaction product. Accordingly, the urethane/acrylic hybrid polymer can be cross linked with a polyaziridine, carbodiimides, epoxies or metal ion cross linkers. An example of a polyaziridine polymer useful herein is pentaerythritol-tris-[β-(aziridinyl)proprianate]. An example of a carbodiimide useful herein 1,3-dicyclohexyl-carbodiimide. The urethane/acrylic hybrid polymer is preferably reacted with an aziridine cross linking agent to form the first material in the composite material employed in this invention.

The second material in the composite material is a particulate solid present in the composite material in an amount in the range of from greater than about 0 to about 50, preferably 10 to about 40 and still more preferably from about 20 to about 30 percent particulate solid by total weight of composite material. The particulate solid can have a size in the range of from about 1 to about 15 and preferably from about 2 to about 5 microns. As explained below in connection with the description of the capsule release mechanism, the particle size of the particulate solid in the composite material is preferably not less than 1 micron. In a manufacturing operation it is, of course, difficult to completely exclude all particulate solids having a size of less than 1 micron, however, it is preferred that concentration of particulate solids having a size less than 1 micron should not exceed about 25 percent by weight of particulate solids present in the composite material.

The second material can include silica, calcium carbonate, titanium dioxide, barium sulfate, calcium sulfate, similar such materials and mixtures thereof.

The first chemical composition encapsulated within the composite material of this invention can be substantially any water-soluble material, limited as previously stated, selected from the group consisting of enzymes, and organic and inorganic acids, bases, salts and oxidizing agents. More specifically, the chemical compositions preferably include alkali, alkaline earth metal and ammonium halides, oxides, hydroxides, carbonates, bicarbonates, perborates, peroxides, percarbonates, bisulfates, bromates and sulfates. The chemical agents can also include liquids which have been adsorbed on solid subtrates, such as, diatomaceous earth and then encapsulated.

Specific examples of chemical agents useful herein as the first chemical composition include hemicellulase, sodium bisulfate, calcium chloride, lithium hydroxides, potassium carbonate, salts of phosphonic acid, sodium persulfate, ammonium persulfate, magnesium oxide, citric acid, fumaric acid, sodium citrate, sodium fumarate, polyglycolic acid, sulfamic acid, potassium bromate, sodium bromate and tetraethylpentamine.

In one embodiment, the first chemical composition can be a breaker for an aqueous fracturing fluid, examples of which include the oxidizing agents, sodium persulfate and potassium persulfate. In another embodiment, the first chemical composition can be an aqueous viscosifying agent such as guar gum, hydroxy propyl guar, hydroxy ethyl cellulose and xanthan gum. In still another preferred embodiment, the first chemical composition can be an additive for adjusting the setting properties of hydraulic cement such as accelerators, retarders and viscosifiers, examples of which include calcium chloride, calcium lignosulfonate and hydroxy ethyl cellulose. In yet another embodiment, the first chemical composition can be a pH adjusting material such as lithium hydroxide and potassium carbonate.

The capsule of this invention can be made by utilizing a fluidized bed process, one version of which is referred to as the Wurster process and a modification thereof which employs a top spray method. Equipment employed to produce the capsule is available from Glatt Air Techniques, Inc. Ramsey, N.J. A specific apparatus available from Glatt Air Techniques is the WSG 5 fluidized bed coater, the use of which is illustrated in the examples set out below.

In a preferred method of manufacture, the capsule of this invention is made by first admixing the second material, the particulate solid, with the first material, the urethane/acrylic hybrid polymer, in the proportions above disclosed. The cross linker can then be admixed with the hybrid polymer and solid in an amount in the range of from about 0 to about 5, and preferably from about 1 to about 3, percent cross linker by weight of hybrid polymer. Thereafter, utilizing the fluidized bed process, the first chemical composition to be encapsulated is introduced into a spray chamber and suspended therein by a flow of gas, such as air, while the mixture of hybrid polymer, solid and cross linker are sprayed against the suspended chemical composition to thereby form the capsule. The combination of chemical composition to be encapsulated and composite material is adjusted to produce a capsule having in the range of from about 10 to about 50, and preferably from about 20 to about 40 percent composite material by weight of capsule.

As previously indicated, the capsules of this invention can be made by well known fluidized bed encapsulation techniques wherein solid particles of the first chemical composition are sprayed with the composite material while the particles are suspended in a flow of air or other gas within a spray chamber. There is no known limitation on the particle size of the chemical composition being encapsulated, but a particle size in the range of from about 10 to about 60 mesh US Sieve series is conveniently employed. Thus, with respect to the above range, particles of a size which do not pass a 10 mesh screen and particles which do pass a 60 mesh screen are preferably not employed. To maintain product uniformity with respect to performance, the first chemical composition, prior to encapsulation, is preferably sized to remove a substantial portion of any fines or agglomerations of chemical particles. In this manner, the thickness of the membrane wall of the capsules will have, within a relatively narrow range, a substantially uniform thickness and the capsules will exhibit generally uniform release control properties.

Generally, the capsule of this invention is prepared having a membrane coating consisting of the cross linked urethane/acrylic hybrid polymer and particulate mixture, i.e. the composite material, of a certain thickness and permeability to obtain the desired controlled release of the first chemical composition for a particular dissolved second chemical composition to be treated. The quantity and size of the particulate present in the composite material will significantly effect the permeability of the created membrane coating.

The particle size of the capsule varies depending upon the desired amount of chemical composition to be released and the desired rate at which the composition is to be released. For example, the thicker the membrane, generally the slower the release since it takes longer for an aqueous liquid in contact with the exterior surface of the capsule to diffuse, i.e., permeate, through the wall of the membrane to dissolve the agent and then diffuse, i.e., permeate, back through the membrane. This relationship, however, can be modified by changing the particle size of the second material present in the matrix. If the second chemical composition to be treated by the first chemical composition is a fracturing fluid containing a proppant, then it is preferred that the particle size of the capsule be substantially equal to or smaller than the particle size the proppant.

In the method of operation, an aqueous liquid in contact with the exterior surface of the capsule gradually passes, by diffusion, through the membrane into the hollow interior of the capsule and therein contacts and dissolves the first chemical composition encapsulated therein to form a solution of the composition in water. It is to be understood that the aqueous solution in contact with the exterior surface of the capsule can be present in the contact location as a natural constituent of the environment or introduced into the environment prior to, together with or subsequent to the introduction of the capsule.

The solution formed within the capsule then gradually passes, by diffusion, from the hollow interior of the capsule through the membrane to the exterior of the capsule to there contact and react with the second chemical composition.

The described operating mechanism, which consists in diffusion of an aqueous liquid in contact with the exterior of the capsule into the capsule and diffusion of a formed solution out of the capsule, requires an extended period of time to be completed to thereby avoid release of all of the first chemical composition over a very short span of time.

It is believed that the operating mechanism of this invention is driven by very small pressure differences between the interior and exterior of a capsule. Thus, when the pressure in the interior of the capsule is less than the pressure on the exterior of the capsule, the aqueous liquid passes through the membrane to the interior of the capsule to contact and dissolve the first chemical composition. Upon dissolution, pressure within the interior of the capsule increases to a value greater than the pressure on the exterior of the capsule. Accordingly, upon this pressure increase, the formed solution passes through the membrane to the exterior of the capsule. In some instances, depending upon the nature of the aqueous liquid and/or the nature of the agent, a gas may be produced within the interior of the capsule. In spite of the described pressure actuated mechanism, it is believed that the pressure stresses do not cause the capsule to rupture, break, dissolve or disintegrate. The capsule remains intact during the entire diffusion process.

The particle size of the second material, which is fixed in the matrix, plays an important role in the diffusion process. In this regard, it is believed that capsules which contain particles having a size of less than about 1 micron, i.e., submicron particles, do not operate to dissipate internal pressure, generated as described above, at a rate sufficiently great to prevent rupture of the capsule. Capsules which contain particles having a size of 2 microns and greater, preferably about 5 microns, fixed in the matrix, do operate to dissipate internal pressure at a rate sufficient to prevent rupture of the capsule.

The capsule of this invention functions to slowly release all of the encapsulated first chemical composition over an extended period of time as contrasted with a rapid release of all of the encapsulated agent over a very short period of time. The capsule operates as stated, without change in the desired rate of release of the encapsulated composition, in the presence of liquids at temperatures in the range of from about 50 to about 325° F. and at pH values in the range of from about 2 to about 11.

The above disclosure has concentrated on the permeable wall of the capsule of this invention as consisting solely of a defined first material or as a composite material consisting of a combination of the first material and a defined particulate second material. However, in another aspect, the membrane of this invention, as defined above, can serve as an undercoat or a primer coat for a third material, such as an acrylic, which would not be compatible with the encapsulated first chemical composition if placed in direct contact therewith. It has been discovered that the membrane of this invention can successfully function as a barrier between an encapsulated chemical and a coating which, for some reason, would not ordinarily be compatible with the encapsulated chemical.

EXAMPLES

The following examples are provided to illustrate the manufacture and use of the invention and to contrast its operation with the prior art.

Example A

Method for Preparing Membrane Material

This invention is a capsule having a permeable wall, referred to as a membrane, and a hollow interior containing a water soluble chemical composition. The membrane is comprised of a first material, previously described as a supporting matrix, which can have fixed therein a second material, previously referred to as a particulate. This example discloses a method of preparing the said first material.

Accordingly, 31.6 pounds of an aqueous polymer dispersion containing 40 percent by weight solids and 60 percent by weight water was introduced into a five gallon container. The solids component of the aqueous polymer dispersion contained 50 percent by weight polyurethane and 50 percent by weight vinyl polymer. Thereafter, 61.0 grams of a silicone surface additive and 74.4 grams of a silicone defoamer were introduced into the container containing the polymer dispersion to form a mixture which was blended with moderate agitation for 15 minutes to form a homogeneous mixture. Then 1004.6 grams of coalescent solvent was added to the homogenous mixture to form the completed mixture and agitation was continued for an additional two hours. The completed mixture, referred to herein as Hybrid Urethane A, contained about 37 percent by weight solids and had a density of about 8.5 pounds per gallon.

The aqueous polymer dispersion used was a product available from Air Products and Chemicals, Inc., under the trademark Hybradur 540, said to be prepared by the process disclosed in U.S. Pat. No. 5,173,526. The silicone defoamer used was identified as BYK-024 available from BYK-Chemie. The silicone surface additive used was identified as BYK-333 available from BYK-Chemie. The coalescent solvent used was identified as glycol ether DPM available from Chem Central.

Example B

Method for Preparing Membrane Material

The procedure described in Example A, above, for preparing Hybrid Urethane A did not include the step of adding a particulate which has been called the second material of the composite material of this invention. This example modifies the procedure of Example A and describes the preparation of four materials, Hybrid Urethane B, Hybrid Urethane C, Hybrid Urethane D and Hybrid Urethane E, each of which includes the first material and the second material of the composite material of this invention.

Accordingly, a blend consisting of quantities of the aqueous polymer dispersion of Example A, the defoamer of Example A and the surface additive of Example A and at least one particulate were combined to form a precursor. Thereafter, a further quantity of the aqueous polymer dispersion of Example A and a quantity of the coalescent solvent of Example A were added to the precursor to complete the preparation of the composite material.

Aqueous polymer dispersion, defoamer and surface additive were introduced into a container of suitable size and moderately agitated to combine the ingredients. Thereafter, the particulate was added with moderate to high agitation for at least about one hour to thoroughly mix all of the combined ingredients to thereby form the precursor. Then, a further quantity of aqueous polymer dispersion was added to the precursor with moderate agitation followed by addition of the coalescent solvent. Agitation was continued for a period of at least about 30 minutes to complete the preparation of the composite material.

The particulates employed were silica, available from US Silica under the identifier MIN-U-SIL 5, and calcium carbonate, available from OMYA, Inc., under the identifier OMYABARB 3T and 4T.

The recipes and physical properties of Hybrid Urethanes B, C, D and E are provided in Tables 1 and 2, respectively, below.

TABLE 1

Recipes for Hybrid Urethanes Containing Particulates
RECIPE FOR COMPOSITE MATERIAL

| | Precursor Content | | | | | Precursor Additives | |
|---|---|---|---|---|---|---|---|
| | basic contents | | | | | basic contents | |
| | aqueous | | | particulates | | aqueous | |
| Hybrid Urethane | polymer dispersion grams | defoamer grams | surface additive grams | silica grams | calcium carbonate grams | polymer dispersion grams | coalescent solvent grams |
| B | 5287.8 | 28.60 | 35.50 | 886.3 | — | 1362.0 | 467.2 |
| C | 5035.6 | 29.10 | 35.40 | — | 879.30 | 1789.1 | 468.7 |
| D | 5314.8 | 34.70 | 42.30 | 867.3 | 218.40 | 2816.5 | 869.7 |
| E | 4041.9 | 61.19 | 74.25 | 1682.9 | 189.84 | 9982.7 | 988.1 |

TABLE 2

Physical Properties of Hybrid Urethanes of Table 1
PHYSICAL DATA

| Hybrid Urethane | Density lb/gal | Solids Concentration % by weight | Viscosity centipoise |
|---|---|---|---|
| B | 9.306 | 44.7 | 176.2 |
| C | 9.148 | 44.8 | 121.2 |
| D | 9.172 | 44.7 | 95.2 |
| E | 9.394 | 44.7 | 175.6 |

Note: The viscosity of the polymer was measured using a Brookfield RVDV 1 viscometer with a #1 spindle rotating at 50 rpm

Example C

Standard Procedure for Preparing Encapsulated Chemical Compositions

In the examples which follow a standard procedure was employed to encapsulate a chemical composition in a membrane. A description of the standard procedure is set out in this example.

Capsules were produced using a WSG 5 fluidized bed coater available from Glatt Air Techniques. The coating was applied using a top spray insert. The spray head used was a Schlick Model 970 spray nozzle available from Orthos Liquid Systems Inc. with a 1.2-mm insert. Depending on the product, either a 80 mesh screen or a 10 micron sock was installed between the expansion chamber and the filter chamber to act as the filter. The air used to fluidize the product was heated in order to maintain a bed temperature in the range of from about 88 to about 106° F. The air used to atomize the coating at the spray head was pressurized to 37 psi. After all of the coating was applied, the bed temperature was allowed to increase to a value in the range of from about 105 to about 110° F. for about five minutes to cure the coating.

Example I

Encapsulation of Lithium Hydroxide

The coating material disclosed in Norman et al (U.S. Pat. No. 5,373,901) was used in an attempt to encapsulate lithium hydroxide. Thus, 628.2 grams of water and 55.8 g of polyaziridine crosslinker were added to 3316.0 grams of the coating material disclosed in Norman et al. The fluidized bed coater of Example C was charged with 7000 grams of anhydrous lithium hydroxide. The lithium hydroxide employed did not include particles which were small enough to pass through a 60 mesh screen. The lithium hydroxide was not successfully encapsulated. Varying the processing conditions did not produce capsules containing lithium hydroxide. It was apparent that lithium hydroxide produced a negative effect on the application of the coating material disclosed by Norman et al.

Example 2

Encapsulation of Lithium Hydroxide

The polyaziridine crosslinker of Example 1 (36.5 grams) and 62.2 grams of water were added to 3651.4 grams of the Hybrid Urethane A of Example A. The resulting mixture was stirred for 10 minutes. The fluidized bed coater of Example C was charged with 5000 grams of anhydrous lithium hydroxide. The lithium hydroxide employed consisted of particles which were small enough to pass through a 10 mesh screen but did not include particles which were small enough to pass through a 50 mesh screen. The bed temperature was maintained at a value in the range of from about 94 to about 100° F. The coating mixture was initially applied at a rate of about 40 g/min, and then increased to a rate of about 52 g/min. A total of 3378.5 grams of coating mixture was successfully added. After the completion of the coating operation it was observed that the lithium hydroxide had experienced an apparent weight increase of approximately 20%, which increase was attributed to the Hybrid Urethane A coating placed thereon.

Example 3

Encapsulation of Lithium Hydroxide

The coating material described in Norman et al (U.S. Pat. No. 5,373,901) was used in an attempt to over coat the capsules produced in Example 2. Thus, 413.0 grams of water and 57.4 grams of the polyaziridine crosslinker of Example 1 were added to 2029.8 grams of the coating material described in Norman et al. The fluidized bed coater of Example C was charged with 4000 grams of the capsules produced in Example 2. The bed temperature was maintained at a value in the range of from about 100 to about 106° F. A total of 2227.2 grams of the coating material of Norman et al was successfully applied resulting in a weight gain of the capsules of approximately 20%.

Example 3, above, illustrates the effectiveness of the Hybrid Urethane A of Example 2 as a primer coat. As shown in Example 1, lithium hydroxide could not be directly coated with the material disclosed in Norman et al, accordingly, a delayed release capsule containing lithium hydroxide directly encapsulated by the material disclosed by Norman et al could not be produced. However, by first coating lithium hydroxide with the Hybrid Urethane A, the resulting capsules could then be coated with the material disclosed by Norman et al. The Hybrid Urethane A thus shielded the material of Norman et al from the lithium hydroxide.

Example 4

The capsules produced in Examples 2 and 3 were contacted with a soak solution consisting of dilute sodium hydroxide at room temperature to cause the release of the encapsulated lithium hydroxide. The soak solution was prepared by dissolving 3.60 grams of sodium hydroxide, 12.0 ml bromocresol green indicator solution and 0.9 ml of nonylphenol surfactant in 900 ml of deionized water. A quantity of encapsulated lithium hydroxide from Example 2 was weighed into a first 125-ml Erlenmeyer flask and an equal quantity of encapsulated lithium hydroxide from Example 3 was weighed into a second 125-ml Erlenmeyer flask. A 5.0 ml quantity of the soak solution was added to each flask. After 10 minutes of exposure a sample of soak solution from each flask was titrated to the end point with 0.5173 M HCl and an additional 5.0 ml soak solution was added. The titration procedure was repeated at intervals of 30 and 60 minutes. The results of the titrations are provided in Table 3.

TABLE 3

| Time | Lithium Hydroxide Released, % | |
|---|---|---|
| minutes | Example 2 | Example 3 |
| 10 | 14.9 | 9.69 |
| 30 | 40.0 | 33.40 |
| 60 | 72.9 | 60.00 |

Example 4 demonstates that the Hybrid Urethane A coating material functions as a primer coat (Example 3) and also as a primary barrier coating (Example 2). It, accordingly, operates in a dual capacity. Since the particles produced in Example 2 included less coating than those produced in Example 3, the rate of release of lithium hydroxide in Example 2 was greater than the rate in Example 3.

Example 5

Encapsulation of Potassium Carbonate

The coating material disclosed in Norman et al was used in an attempt to encapsulate potassium carbonate. Thus, 1011.5 grams of water were added to 5988.5 grams of the coating material disclosed in Norman et al. The fluidized bed coater of Example C was charged with 9000 grams of potassium carbonate. The potassium carbonate employed did not include particles which were small enough to pass through a 40 mesh screen. The potassium carbonate was not successfully encapsulated. Varying the processing conditions did not produce capsules containing potassium carbonate. It was apparent that potassium carbonate produced a negative effect on the application of the coating material disclosed by Norman et al.

Example 6

Encapsulation of Potassium Carbonate

The polyaziridine crosslinker of Example 1 (31.2 grams) and 53.0 grams of water were added to 3124.0 grams of the Hybrid Urethane A of Example A. The resulting mixture was stirred for 10 minutes. The fluidized bed coater of Example C was charged with 7000 grams of potassium carbonate. The potassium carbonate employed consisted of particles which were small enough to pass through a 10 mesh screen but did not include particles which were small enough to pass through a 60 mesh screen. The bed temperature was maintained at a value in the range of from about 100 to about 105° F. The coating mixture was applied at a rate of about 40 g/min. A total of 3082.0 grams of coating mixture was successfully added. After the completion of the coating operation it was observed that the potassium carbonate had experienced an apparent weight increase of approximately 16%, which increase was attributed to the Hybrid Urethane A coating placed thereon.

Example 7

Encapsulation of Potassium Carbonate

The coating material described in Norman et al (U.S. Pat. No. 5,373,901) was used in an attempt to over coat the capsules produced in Example 6. Thus, 1036.6 grams of water and 92.1 grams of the polyaziridine crosslinker of Example 1 were added to 5471.3 grams of the coating material described in Norman et al. The fluidized bed coater of Example C was charged with 6500 grams of the capsules produced in Example 6. The bed temperature was maintained at a value in the range of from about 100 to about 106° F. A total of 6,190.5 grams of the coating material of Norman et al was successfully applied resulting in a weight gain of the capsules of approximately 30%.

Example 7, above, illustrates the effectiveness of the Hybrid Urethane A of Example 6 as a primer coat. As shown in Example 5, potassium carbonate could not be directly coated with the material disclosed in Norman et al. Accordingly, a delayed release capsule containing potassium carbonate directly encapsulated by the material disclosed by Norman et al could not be produced. However, by first coating potassium carbonate with the Hybrid Urethane A, the resulting capsules could then be coated with the material disclosed by Norman et al. The Hybrid Urethane A thus shielded the material of Norman et al from the potassium carbonate.

Example 8

The capsules produced in Examples 6 and 7 were contacted with a soak solution at temperatures of 75 and 150° F. to cause the release of the encapsulated potassium carbonate. The soak solution was prepared by dissolving 4 drops of bromocresol green indicator solution and 0.1% of nonylphenol surfactant in 10 ml of deionized water. A quantity of encapsulated potassium carbonate from Example 6 was weighed into a first 50-ml Erlenmeyer flask and an equal quantity of encapsulated potassium carbonate from Example 7 was weighed into a second 50-ml Erlenmeyer flask. At the indicated times, the samples were titrated to the end point with 0.5055 M HCl. The results of the titrations are provided in Table 4.

TABLE 4

| Time | Potassium Carbonate Released, % | | | |
|---|---|---|---|---|
| | 75° F. | | 150° F. | |
| minutes | Example 6 | Example 7 | Example 6 | Example 7 |
| 20 | 23.0 | 0.99 | 51.2 | 6.22 |
| 40 | 43.0 | 2.04 | 77.7 | 19.50 |
| 60 | 60.3 | 3.70 | 88.4 | 36.70 |
| 90 | 73.1 | 5.58 | 94.0 | 63.80 |
| 120 | 80.5 | 7.57 | 95.3 | 82.70 |
| 180 | 88.2 | 11.5 | 96.0 | 95.30 |
| 240 | 91.7 | 14.4 | — | — |

Example 8 demonstrates that the Hybrid Urethane A coating material functions as a primer coat (Example 7) and also as a primary barrier coating (Example 6). It, accordingly, operates in a dual capacity. Since the particles produced in Example 6 included less coating than those produced in Example 7, the rate of release of potassium carbonate in Example 6 was greater than the rate in Example 7. Example 8 further demonstrates that increase in temperature of contact increases the rate of release of encapsulated material

Example 9

Encapsulation of Magnesium Oxide

The polyaziridine crosslinker of Example 1 (40.8 grams) and 69.5 grams of water were added to 4089.6 grams of the Hybrid Urethane A of Example A. The resulting mixture was stirred for 10 minutes. The fluidized bed coater of Example C was charged with 7000 grams of prilled magnesium oxide. The bed temperature was maintained at a value in the range of from about 88 to about 95° F. The coating mixture was applied at a rate of about 60 g/min.

In one run a total of 1217.5 grams of coating mixture was successfully added. In a second run a total of 4187.1 grams of coating mixture was successfully added. After the completion of the coating operation it was observed that the magnesium oxide had experienced an apparent weight increase of approximately 6% in the first run and approximately 18% in the second run. The weight increase was attributed to the Hybrid Urethane A coating placed thereon.

Example 10

To determine the effectiveness of the coated materials prepared in Example 9, samples were tested by observing the pH change of aqueous solutions containing active magnesium oxide. In this regard, 2.13 grams of the 6% material and 2.44 grams of the 18% material as prepared in Example 9 were employed, each of which contained 2.00 grams of active magnesium oxide. These two samples were compared with 2.00 grams of un-coated magnesium oxide. Accordingly, 100 ml of deionized water containing 1% nonylphenol surfactant was placed into each of three 250 ml beakers equipped with a stirring bar. The beakers were placed in turn on a stirring plate and a temperature compensated pH probe was immersed into the solution in each beaker. After the pH stabilized, a 2.00 gram active MgO sample was added to each beaker. The pH of the solution in each beaker was recorded versus time. The results of the pH measurements are provided in Table 5.

TABLE 5

| Time | pH of Solution Coating % | | |
|---|---|---|---|
| minutes | 0 | 6 | 18 |
| 0.0 | 5.00 | 6.02 | 4.85 |
| 0.5 | 8.90 | 6.20 | 4.81 |
| 1.0 | 9.28 | 6.41 | 4.83 |
| 2.0 | 9.87 | 6.92 | 4.92 |
| 3.0 | 10.33 | 7.67 | 4.96 |
| 4.0 | 10.54 | 8.16 | 5.02 |
| 5.0 | 10.66 | 8.36 | 4.87 |
| 7.0 | 10.78 | 8.80 | 5.04 |
| 10.0 | 10.89 | 9.00 | 5.06 |
| 15.0 | 11.00 | 9.32 | 5.50 |
| 30.0 | 11.16 | 9.79 | 5.47 |
| 60.0 | 11.23 | 10.12 | 5.97 |
| 90.0 | | 10.29 | 6.25 |
| 120.0 | | 10.31 | 6.36 |
| 180.0 | | | 6.95 |

The results obtained in Example 10, above, demonstrate the Hybrid Urethane A operates as a barrier coating for magnesium oxide.

Example 11

Encapsulation of Ammonium Persulfate

The polyaziridine crosslinker of Example 1 (42.3 grams) and 96.0 grams of water were added to 4262.0 grams of the Hybrid Urethane A of Example A. The resulting mixture was stirred for 10 minutes. The fluidized bed coater of Example C was charged with 7000 grams of ammonium persulfate. The ammonium persulfate employed consisted of particles which were small enough to pass through a 20 mesh screen but did not include particles which were small enough to pass through a 50 mesh screen. The bed temperature was maintained at a value in the range of from about 100 to about 105° F. The coating mixture was applied at a rate of in the range of from about 40 to about 60 g/min. A total of 4170.6 grams of coating mixture was successfully added. After the completion of the coating operation it was observed that the ammonium persulfate had experienced an apparent weight increase of approximately 18%, which increase was attributed to the Hybrid Urethane A coating placed thereon.

The coated particles produced as described above were further treated to increase the weight increase to a total of 36%. Accordingly, to 4649.4 grams of Hybrid Urethane A was added 46.3 grams of polyaziridine crosslinker and 95.0 grams of water. The resulting mixture was stirred for 10 minutes. The fluidized bed coater was charged with 6000 grams of the particles as prepared above. The bed temperature was maintained at a value in the range of from about 99 to about 105° F. The coating material was applied at a rate in the range of from about 60 to about 70 g/min. A total of 4559.9 grams of coating material was added resulting in a weight gain of approximately 36%.

Example 12

Encapsulation of Ammonium Persulfate

The polyaziridine crosslinker of Example 1 (33.2 grams) and 96.4 grams of water were added to 3571.1 grams of the Hybrid Urethane E of Example B. The resulting mixture was stirred for 10 minutes. The fluidized bed coater of Example C was charged with 5000 grams of ammonium persulfate. The ammonium persulfate employed consisted of particles which were small enough to pass through a 20 mesh screen but did not include particles which were small enough to pass through a 40 mesh screen. The bed temperature was maintained at a value in the range of from about 93 to about 98° F. The coating mixture was applied at a rate of in the range of from about 60 to about 76 g/min. A total of 2842.3 grams of coating mixture was successfully added. After the completion of the coating operation it was observed that the ammonium persulfate had experienced an apparent weight increase of approximately 20%, which increase was attributed to the Hybrid Urethane E coating material placed thereon.

The coated particles produced as described above were further treated to increase the weight increase to a total of 28%. Accordingly, to 1351.6 grams of Hybrid Urethane E were added 12.3 grams of polyaziridine crosslinker and 36.1 grams of water. The resulting mixture was stirred for 10 minutes. The fluidized bed coater was charged with 5200 grams of the particles as prepared above. The bed temperature was maintained at a value in the range of from about 93 to about 98° F. The coating material was applied at a rate of from about 76 g/min. A total of 1313.6 grams of coating material was added resulting in a weight gain of approximately 28%.

The coated particles produced as described above were further treated to increase the weight increase to a total of 36%. Accordingly, to 1448.2 grams of Hybrid Urethane E was added 13.2 grams of polyaziridine crosslinker and 38.6 grams of water. The resulting mixture was stirred for 10 minutes. The fluidized bed coater was charged with 5000 grams of the particles as prepared above. The bed temperature was maintained at a value in the range of from about 93 to about 98° F. The coating material was applied at a rate of from about 76 g/min. A total of 1421.8 grams of coating material was added resulting in a weight gain of approximately 36%.

Example 13

Release tests were performed with the capsules produced in Example 11 and Example 12, above, and the results were compared with results obtained with capsules of coated ammonium persulfate obtained following the procedure disclosed in Norman et al. The test procedure disclosed in Example II of the Norman et al was employed in the performance of the tests in this example. The test results are recorded in Table 6.

TABLE 6

| Time | Ammonium Persulfate Released, % | | |
|---|---|---|---|
| hours | Example 11 | Example 12 | U.S. Pat. No. 5,373,901 |
| 0.5 | 0.41 | — | 0.88 |
| 1.0 | 1.69 | 7.47 | 2.08 |
| 2.0 | 6.42 | 16.20 | 13.00 |
| 3.0 | 15.40 | — | 53.70 |
| 3.5 | — | 46.80 | — |
| 4.0 | 28.20 | — | 70.80 |
| 4.5 | — | 59.50 | — |
| 5.0 | 37.70 | — | 74.30 |
| 6.0 | 46.00 | — | 76.20 |
| 7.0 | 52.30 | — | — |

The above data clearly illustrates the usefulness of Hybrid Urethane E as a barrier coating for ammonium persulfate and the improved release profiles as compared to that obtained by employing the coating material of U.S. Pat. No. 5,373,901 to Norman et al.

Example 14

Encapsulation of Sulfamic Acid

The polyaziridine crosslinker of Example 1 (37.7 grams) and 49.9 grams of water were added to 4113.3 grams of the Hybrid Urethane A of Example A. The resulting mixture was stirred for 10 minutes. The fluidized bed coater of Example C was charged with 5500 grams of sulfamic acid. The sulfamic acid employed consisted of particles which were small enough to pass through a 10 mesh screen but did not include particles which were small enough to pass through a 50 mesh screen. The bed temperature was maintained at a value in the range of from about 93 to about 98° F. The coating mixture was applied at a rate of in the range of from about 40 to about 55 g/min. A total of 3716.2 grams of coating mixture was successfully added. After the completion of the coating operation it was observed that the sulfamic acid had experienced an apparent weight increase of approximately 20%, which increase was attributed to the Hybrid Urethane A coating material placed thereon.

The coated particles produced as described above were further treated to increase the weight increase to a total of 28%. Accordingly, to 1351.6 grams of Hybrid Urethane A were added 12.3 grams of polyaziridine crosslinker and 36.1 grams of water. The resulting mixture was stirred for 10 minutes. The fluidized bed coater was charged with 5000 grams of the particles as prepared above. The bed temperature was maintained at a value in the range of from about 93 to about 98° F. The coating material was applied at a rate of from about 60 g/min. A total of 1356.0 grams of coating material was added resulting in a weight gain of approximately 28%.

The coated particles produced as described above were further treated to increase the weight increase to a total of 36%. Accordingly, to 1448.2 grams of Hybrid Urethane A was added 13.2 grams of polyaziridine crosslinker and 38.6 grams of water. The resulting mixture was stirred for 10 minutes. The fluidized bed coater was charged with 4300 grams of the particles as prepared above. The bed temperature was maintained at a value in the range of from about 93 to about 98° F. The coating material was applied at a rate of from about 60 g/min. A total of 1414.5 grams of coating material was added resulting in a weight gain of approximately 36%.

Example 15

Encapsulation of Sulfamic Acid

The polyaziridine crosslinker of Example 1 (14.1 grams) and 41.2 grams of water were added to 1544.7 grams of the Hybrid Urethane B of Example B. The resulting mixture was stirred for 10 minutes. The fluidized bed coater of Example C was charged with 5000 grams of sulfamic acid. The sulfamic acid employed consisted of particles which were small enough to pass through a 10 mesh screen but did not include particles which were small enough to pass through a 50 mesh screen. The bed temperature was maintained at a value in the range of from about 93 to about 98° F. The coating mixture was applied at a rate of in the range of from about 50 to about 70 g/min. A total of 1516.2 grams of coating mixture was successfully added. After the completion of the coating operation it was observed that the sulfamic acid had experienced an apparent weight increase of approximately 12%, which increase was attributed to the Hybrid Urethane A coating material placed thereon.

The coated particles produced as described above were further treated to increase the weight increase to a total of 20%. Accordingly, to 1158.5 grams of Hybrid Urethane B were added 10.6 grams of polyaziridine crosslinker and 30.9 grams of water. The resulting mixture was stirred for 10 minutes. The fluidized bed coater was charged with 5000 grams of the particles as prepared above. The bed temperature was maintained at a value in the range of from about 93 to about 98° F. The coating material was applied at a rate of from about 70 g/min. A total of 1113.4 grams of coating material was added resulting in a weight gain of approximately 20%.

The coated particles produced as described above were further treated to increase the weight increase to a total of 28%. Accordingly, to 1158.5 grams of Hybrid Urethane B was added 10.6 grams of polyaziridine crosslinker and 30.9 grams of water. The resulting mixture was stirred for 10 minutes. The fluidized bed coater was charged with 4700 grams of the particles as prepared above. The bed temperature was maintained at a value in the range of from about 93 to about 98° F. The coating material was applied at a rate of from about 70 g/min. A total of 1160.25 grams of coating material was added resulting in a weight gain of approximately 28%.

Example 16

Encapsulation of Sulfamic Acid

The polyaziridine crosslinker of Example 1 (14.1 grams) and 40.2 grams of water were added to 1544.7 grams of the Hybrid Urethane C of Example B. The resulting mixture was stirred for 10 minutes. The fluidized bed coater of Example C was charged with 5000 grams of sulfamic acid. The sulfamic acid employed consisted of particles which were small enough to pass through a 10 mesh screen but did not include particles which were small enough to pass through a 50 mesh screen. The bed temperature was maintained at a value in the range of from about 93 to about 98° F. The coating mixture was applied at a rate of in the range of from about 50 to about 70 g/min. A total of 1519.5 grams of coating mixture was successfully added. After the completion of the coating operation it was observed that the sulfamic acid had experienced an apparent weight increase of approximately 12%, which increase was attributed to the Hybrid Urethane C coating material placed thereon.

The coated particles produced as described above were further treated to increase the weight increase to a total of 20%. Accordingly, to 1158.5 grams of Hybrid Urethane C were added 10.6 grams of polyaziridine crosslinker and 39.9 grams of water. The resulting mixture was stirred for 10 minutes. The fluidized bed coater was charged with 4500 grams of the particles as prepared above. The bed temperature was maintained at a value in the range of from about 93 to about 98° F. The coating material was applied at a rate of from about 70 g/min. A total of 1113.8 grams of coating material was added resulting in a weight gain of approximately 20%.

The coated particles produced as described above were further treated to increase the weight increase to a total of 28%. Accordingly, to 1158.5 grams of Hybrid Urethane C was added 10.6 grams of polyaziridine crosslinker and 30.9 grams of water. The resulting mixture was stirred for 10 minutes. The fluidized bed coater was charged with 4700 grams of the particles as prepared above. The bed temperature was maintained at a value in the range of from about 93 to about 98° F. The coating material was applied at a rate of from about 70 g/min. A total of 1160.2 grams of coating material was added resulting in a weight gain of approximately 28%.

Example 17

Encapsulation of Sulfamic Acid

The polyaziridine crosslinker of Example 1 (25.5 grams) and 74.7 grams of water were added to 2799.8 grams of the Hybrid Urethane D of Example B. The resulting mixture was stirred for 10 minutes. The fluidized bed coater of Example C was charged with 5000 grams of sulfamic acid. The sulfamic acid employed consisted of particles which were small enough to pass through a 10 mesh screen but did not include particles which were small enough to pass through a 50 mesh screen. The bed temperature was maintained at a value in the range of from about 92 to about 98° F. The coating mixture was applied at a rate of in the range of from about 60 to about 76 g/min. A total of 2770.0 grams of coating mixture was successfully added. After the completion of the coating operation it was observed that the sulfamic acid had experienced an apparent weight increase of approximately 20%, which increase was attributed to the Hybrid Urethane D coating material placed thereon.

The coated particles produced as described above were further treated to increase the weight increase to a total of 28%. Accordingly, to 1351.6 grams of Hybrid Urethane D were added 12.3 grams of polyaziridine crosslinker and 36.1 grams of water. The resulting mixture was stirred for 10 minutes. The fluidized bed coater was charged with 5000 grams of the particles as prepared above. The bed temperature was maintained at a value in the range of from about 93 to about 98° F. The coating material was applied at a rate of about 70 g/min. A total of 1237.5 grams of coating material was added resulting in a weight gain of approximately 28%.

Example 18

The capsules produced in Examples 14, 15, 16 and 17 were contacted with a soak solution to cause the release of the encapsulated sulfamic acid. The soak solution was prepared by adding 0.15 grams of phenolphthalein in 15 ml of isopropyl alcohol, and 0.1 ml of nonylphenol surfactant to 1000 ml of deionized water.

A quantity of encapsulated sulfamic acid produced in Example 14 was weighed into a first 125-ml Erlenmeyer flask. A quantity of encapsulated sulfamic acid produced in Example 15 (equal to the quantity from Example 14) was weighed into a second 125-ml Erlenmeyer flask. A quantity of encapsulated sulfamic acid produced in Example 16 (equal to the quantity from Example 14) was weighed into a third 125-ml Erlenmeyer flask. A quantity of encapsulated sulfamic acid produced in Example 17 (equal to the quantity from Example 14) was weighed into a fourth 125-ml Erlenmeyer flask.

The soak solution in an amount of 20 ml was then added to each of the four flasks. The contents of each flask were then titrated to the end point with 0.5 M NaOH at the times indicated in Table 7. The results of the titrations are provided in Table 7.

TABLE 7

| Time | Sulfamic Acid Released, % | | | |
|---|---|---|---|---|
| hrs:min | Example 14 | Example 15 | Example 16 | Example 17 |
| 0:10 | 5.18 | 9.27 | 9.93 | 8.84 |
| 0:20 | 7.55 | 13.10 | 13.5 | 12.70 |
| 0:40 | 11.10 | 20.82 | — | 20.20 |
| 1:00 | 14.80 | 26.00 | — | 26.60 |
| 2:00 | 22.00 | 37.00 | — | 39.60 |
| 3:00 | 27.90 | 43.40 | — | — |
| 4:00 | 32.20 | 48.60 | — | — |
| 5:00 | 36.90 | 52.40 | — | — |
| 7:30 | 43.20 | 59.70 | — | — |
| overnight | 63.90 | 77.50 | — | 82.7 |

The above data clearly illustrates the usefulness of Hybrid Urethanes A, B, C and D as barrier coatings for sulfamic acid.

Example 19

Encapsulation of Sodium Bromate

The polyaziridine crosslinker of Example 1 (48.0 grams) and 60.2 grams of water were added to 4086.5 grams of the Hybrid Urethane A of Example A. The resulting mixture was stirred for 10 minutes. The fluidized bed coater of Example C was charged with 6000 grams of sodium bromate. The sodium bromate consisted of particles which were small enough to pass through a 10 mesh screen but did not include particles which were small enough to pass through a 40 mesh screen. The bed temperature was maintained at a value in the range of from about 93 to about 98° F. The coating mixture was applied at a rate in the range from about 40 to about 60 g/min. A total of 3465.0 grams of coating mixture was successfully added. After the completion of the coating operation it was observed that the sodium bromate had experienced an apparent weight increase of approximately 18%, which increase was attributed to the Hybrid Urethane A coating placed thereon.

Example 20

Encapsulation of Sodium Bromate

The polyaziridine crosslinker of Example 1 (37.2 grams) and 122.9 grams of water were added to 4042.0 grams of the Hybrid Urethane E of Example B. The resulting mixture was stirred for 10 minutes. The fluidized bed coater of Example C was charged with 7000 grams of sodium bromate. The sodium bromate employed consisted of particles which were small enough to pass through a 10 mesh screen but did not include particles which were small enough to pass through a 40 mesh screen. The bed temperature was maintained at a value in the range of from about 98 to about 103° F. The coating mixture was applied at a rate of in the range of from about 48 to about 62 g/min. A total of 3603.0 grams of coating mixture was successfully added. After the completion of the coating operation it was observed that the sodium bromate had experienced an apparent weight increase of approximately 18.3%, which increase was attributed to the Hybrid Urethane E coating material placed thereon.

The coated particles produced as described above were further treated to increase the weight increase to a total of 36%. Accordingly, to 3751.5 grams of Hybrid Urethane E were added 34.3 grams of polyaziridine crosslinker and 114.1 grams of water. The resulting mixture was stirred for 10 minutes. The fluidized bed coater was charged with 5200 grams of the particles as prepared above. The bed temperature was maintained at a value in the range of from about 98 to about 103° F. The coating material was applied at a rate of about 62 g/min. A total of 3077.8 grams of coating material was added resulting in a weight gain of approximately 36%.

Example 21

Encapsulation of Sodium Bromate

The coating material disclosed in Norman et al (U.S. Pat. No. 5,373,901) was used in an attempt to encapsulate sodium bromate. Thus, 596.4 grams of water and 83.3 g of polyaziridine crosslinker were added to 2923.8 grams of the coating material disclosed in Norman et al. The fluidized bed coater of Example C was charged with 5000 grams of sodium bromate. The sodium bromate employed consisted of particles which were small enough to pass through a 10 mesh screen but did not include particles which were small enough to pass through a 50 mesh screen. The bed temperature was maintained at a value in the range of from about 100 to about 106° F. The coating mixture was applied at a rate of in the range of from about 60 to about 76 g/min. A total of 2777.6 grams of coating mixture was successfully added. After the completion of the coating operation it was observed that the sodium bromate had experienced an apparent weight increase of approximately 20% which increase was attributed to the coating material disclosed in Norman et al placed thereon.

Example 22

Capsules produced in Examples 19, 20 and 21 were contacted with 50 ml of a preheated soak solution consisting of 0.1% nonylphenol surfactant in deionized water to cause the release of the encapsulated sodium bromate. A quantity 1.5 grams of encapsulated sodium bromate was weighed and then added to the soak solution which was contained in a 2 oz jar. The test sample was allowed to stand with periodic swirling. At the times indicated in the tables below a 5.0 ml aliquot was removed and transferred to a 125 ml Erlenmeyer flask containing about 20 ml of deionized water. To the flask was added 2.0 grams of potassium iodide and 5 ml of 6N HCl. The mixture was immediately titrated to a starch-iodine end point with standardized sodium thiosulfate solution. The results of the titrations are reported in Tables 8 and 9.

TABLE 8

| Time | Sodium Bromate Released, % Test Temperature 75° F. | | |
|---|---|---|---|
| hours | Example 19 | Example 20 | Example 21 |
| 0.25 | 1.61 | 0.25 | 2.13 |
| 1.00 | 13.20 | 0.45 | 7.61 |
| 2.00 | 27.30 | — | — |
| 3.00 | — | 13.20 | — |
| 4.00 | 53.20 | — | — |
| 6.00 | — | 30.90 | — |

TABLE 9

| EXAMPLE 20 | | | |
|---|---|---|---|
| Time | Sodium Bromate Released, % | | |
| hours | 75° F. | 125° F. | 150° F. |
| 0.25 | 0.25 | 0.20 | 0.10 |
| 1.00 | 0.45 | 0.18 | 0.14 |
| 3.00 | 13.20 | 0.40 | 0.44 |
| 6.00 | 30.91 | 3.46 | 7.07 |
| 22.00 | 91.80 | 76.20 | 81.60 |

The above data clearly illustrate the usefulness of Hybrid Urethane A and Hybrid Urethane E as barrier coatings for sodium bromate and show an improved release profile as compared to capsules produced according to U.S. Pat. No. 5,373,901.

Having described the invention that which is claimed is:

1. An article of manufacture comprising a capsule and a first chemical composition, said capsule having a hollow interior and an enclosing membrane wall having an interior surface and an exterior surface, wherein said first chemical composition is enclosed within said hollow interior of said capsule;

said membrane is permeable to water and aqueous solutions, but is not soluble in aqueous liquids, and includes at least a first material comprised of a polyurethane-vinyl polymer dispersion prepared by the simultaneous polymerization of a vinyl monomer and chain extension of an isocyanate-terminated polyurethane prepolymer in the presence of water to thereby form a urethane/vinyl hybrid polymer; and said first chemical composition is comprised of a solid, water-soluble chemical composition which is not reactive with, soluble in or a solvent for said membrane.

2. The article of claim 1 wherein said first chemical composition is selected from the group consisting of alkali, alkaline earth metal and ammonium halides, oxides, hydroxides, carbonates, bicarbonates, perborates, peroxides, percarbonates, bisulfates and persulfates.

3. The article of claim 2 wherein said membrane is a composite material comprised of said first material and further comprised of a second material, wherein said first material is a supporting matrix for said second material which is fixed in said supporting matrix;

said second material is a particulate solid, having a particle size in the range of from about 1 to about 15 microns, present in said composite material in an amount in the range of from an amount greater than about 0 to about 50 percent of said particulate solid by total weight of said composite material;

said second material is different from said first material, and is not reactive with, soluble in or a solvent for said first material or said first chemical composition; and said composite material is present in said article in an amount in the range of from about 10 to about 50 percent by weight of said composite material by weight of said article.

4. The article of claim 2 wherein said first material is reacted with a cross linking agent selected from the group consisting of polyaziridines, carbodiimides, epoxies and metal ion cross linkers.

5. The article of claim 3 wherein said second material is selected from the group consisting of silica, calcium carbonate, titanium dioxide, barium sulfate, calcium sulfate and mixtures thereof.

6. The article of claim 2 wherein said first chemical composition has a particle size in the range of from about 10 to about 60 mesh US Sieve series.

7. The article of claim 5 wherein said first material is reacted with a cross linking agent selected from the group consisting of polyaziridines, carbodiimides, epoxies and metal ion cross linkers.

8. The article of claim 5 wherein said first chemical composition has a particle size in the range of from about 10 to about 60 mesh US Sieve series.

9. The article of claim 4 wherein said cross linking agent is a polyaziridine.

10. The article of claim 7 wherein said cross linking agent is a polyaziridine.

11. The article of claim 4 wherein said first chemical composition has a particle size in the range of from about 10 to about 60 mesh US Sieve series.

12. The article of claim 7 wherein said first chemical composition has a particle size in the range of from about 10 to about 60 mesh US Sieve series.

13. The article of claim 7 wherein said second material is silica.

14. The article of claim 7 wherein said second material is calcium carbonate.

15. The article of claim 13 wherein said cross linking agent is a polyaziridine.

16. The article of claim 13 wherein said cross linking agent is a carbodiimide.

17. The article of claim 14 wherein said cross linking agent is a carbodiimide.

18. The article of claim 5 wherein said first material is reacted with a polyaziridine cross linking agent.

19. The article of claim 6 wherein said first material is reacted with a polyaziridine cross linking agent.

* * * * *